US008114455B2

(12) United States Patent
Paulsen et al.

(10) Patent No.: US 8,114,455 B2
(45) Date of Patent: *Feb. 14, 2012

(54) PROCESS FOR MANUFACTURING CHEWABLE DOSAGE FORMS FOR DRUG DELIVERY AND PRODUCTS THEREOF

(75) Inventors: Neil E. Paulsen, Johns Island, SC (US);
Roland Johnson, Lexington, NC (US);
Michael Coffee, Greensboro, NC (US)

(73) Assignee: Bayer B.V., Mijdrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/115,919

(22) Filed: May 25, 2011

(65) Prior Publication Data
US 2011/0223234 A1 Sep. 15, 2011

Related U.S. Application Data

(63) Continuation of application No. 11/940,106, filed on Nov. 14, 2007, now Pat. No. 7,955,632, which is a continuation-in-part of application No. 11/296,181, filed on Dec. 7, 2005, now abandoned.

(51) Int. Cl.
*A23G 3/02* (2006.01)
*A23K 1/17* (2006.01)
*A61K 47/00* (2006.01)
*A61K 9/14* (2006.01)

(52) U.S. Cl. ........ 426/514; 424/439; 424/442; 424/489; 426/392; 426/418; 426/422; 426/442; 426/512

(58) Field of Classification Search ........................ None
See application file for complete search history.

(56) References Cited

U.S. PATENT DOCUMENTS

| | | |
|---|---|---|
| 3,486,186 A | 12/1969 | Richards et al. |
| 3,887,964 A | 6/1975 | Richards |
| 3,952,478 A | 4/1976 | Richards et al. |
| 4,054,967 A | 10/1977 | Sandberg et al. |
| 4,097,961 A | 7/1978 | Richards |
| 4,182,003 A | 1/1980 | Lamartino et al. |
| 4,306,883 A | 12/1981 | Eckman |
| 4,334,339 A | 6/1982 | Holly |
| 4,338,702 A | 7/1982 | Holly |
| 4,343,068 A | 8/1982 | Holly |
| 4,356,595 A | 11/1982 | Sandberg et al. |
| 4,372,008 A | 2/1983 | Sandberg |
| 4,535,505 A | 8/1985 | Holly et al. |
| 4,597,135 A | 7/1986 | Holly et al. |
| 4,608,731 A | 9/1986 | Holly |
| 4,622,717 A | 11/1986 | Bollinger |
| 4,697,308 A | 10/1987 | Sandberg |
| 4,710,390 A | 12/1987 | Schumacher et al. |
| 4,724,150 A | 2/1988 | Knebl et al. |
| 4,768,941 A | 9/1988 | Wagner |
| 4,780,931 A | 11/1988 | Powers et al. |
| 4,800,087 A | 1/1989 | Mehta |
| 4,818,446 A | 4/1989 | Schreiber et al. |
| 4,821,376 A | 4/1989 | Sandberg |
| 4,872,241 A | 10/1989 | Lindee |
| 4,975,039 A | 12/1990 | Dare et al. |
| 4,996,743 A | 3/1991 | Janssen |
| 5,021,025 A | 6/1991 | Wagner |
| 5,022,888 A | 6/1991 | Lindee |
| 5,320,848 A | 6/1994 | Geyer et al. |
| 5,380,535 A | 1/1995 | Geyer et al. |
| 5,637,313 A | 6/1997 | Chau et al. |
| 5,655,436 A | 8/1997 | Soper |
| 5,735,603 A | 4/1998 | Kesig et al. |
| 5,747,061 A | 5/1998 | Amselem et al. |
| 5,980,228 A | 11/1999 | Soper |
| 6,340,471 B1 | 1/2002 | Kershman et al. |
| 6,344,222 B1 | 2/2002 | Cherukuri et al. |
| 6,613,346 B2 | 9/2003 | Seielstad et al. |
| 6,672,252 B2 | 1/2004 | Levin et al. |
| 6,777,401 B2 | 8/2004 | Hanna |
| 6,868,136 B2 | 3/2005 | Hansen et al. |

FOREIGN PATENT DOCUMENTS

| | | |
|---|---|---|
| EP | 1 675 474 B1 | 10/2008 |
| WO | WO 2005/094210 | 10/2005 |

OTHER PUBLICATIONS

Article entitled "Fluidized Bed Mixing Techniques," published online Feb. 2, 2001, website address: http://www.chemicalonline.com/article.mvc/Fluidized-Bed-Mixing-Technique-00001.
Balabudkin et al., "Improvement in the Technology of Manufacturing Ointments Containing Antibiotics," (1979), Plenum Publishing Corporation.
Chung et al., "Frictional Behavior of Solid Polymers on a Metal Surface at Processing Conditions," *Polymer Engineering and Science* (1977), 17:9-20.
Derezinski, S., "The Compressibility of the Resin Solid Feed Bed in Extrusion," *Conference Proceedings, ANTEC '88, Society of Plastics Engineers* (1988), 105-108. Derezinski et al., "Heat Transfer Coefficients in Extruder Melt Sections," *Conference Proceedings, ANTEC '96, Society of Plastics Engineers* (1996), 417-421.
Derezinski, Stephen J., "Calculating Power of Extruder Melt Sections," *Journal of Materials Processing & Manufacturing Science* (1997), 6:71-77.
Forberg Fluidized Zone Mixers Manual, American Process Systems, Apr. 1999 Ed.
Handbook of Pharmaceutical Excipients; *American Pharmaceutical Association*, Ascorbic Acid (1986), 6-8.
Handbook of Pharmaceutical Excipients; *American Pharmaceutical Association*, Glycerin (1986), 123.
Lindt, J.T., "Mathematical Modeling of Melting Polymers in Single-Screw Extruders: A Critical Review," *Conference Proceedings, ANTEC '84, Society of Plastics Engineers* (1984), 73-76.
Miller and White, "Heat Transfer in the Transition Section of a Plasticating Extruder," *Conference Proceedings, ANTEC '74, Society of Plastics Engineers* (1974), 243-246.
Mount III et al., "Analytical Melting Model for Extrusion: Melting Rate of Fully Compacted Solid Polymers," *Polymer Engineering and Science* (1982), 22(12):729-737.
Paulsen, Neil, Declaration, Apr. 1, 2009.
Rauwendaal, C., "Dispersed Solids Melting Theory," *Conference Proceedings, ANTEC '93, Society of Plastics Engineers* (1993), 2232-2237.
Vermeulen et al., "The Melting of a Crystalline Polymer in a Screw Extruder," *Chemical Engineering Science* (1971), 26:1457-1465, Pergamon Press.

*Primary Examiner* — Robert A Wax
*Assistant Examiner* — Jeffrey T Palenik
(74) *Attorney, Agent, or Firm* — DLA Piper LLP (US)

(57) ABSTRACT

A palatable, edible soft chewable medication vehicle for delivery of a pharmaceutically acceptable active ingredient, such as a drug, to an animal or human subject. The edible soft chews contain only food grade or better inactive ingredients, and preferably do not contain ingredients of animal origin. Processes for manufacturing the edible soft chews do not require the use of heat or the addition of water during mixing of active and inactive ingredients, provide stable concentrations of the active ingredient, and produce chews of consistent weight and texture.

17 Claims, No Drawings

PROCESS FOR MANUFACTURING CHEWABLE DOSAGE FORMS FOR DRUG DELIVERY AND PRODUCTS THEREOF

CROSS REFERENCE TO RELATED APPLICATIONS

This application is a continuation application of U.S. application Ser. No. 11/940,106 filed Nov. 14, 2007, now issued as U.S. Pat. No. 7,955,632; which is a continuation-in-part application of U.S. application Ser. No. 11/296,181 filed Dec. 7, 2005, now abandoned. The disclosure of each of the prior applications is considered part of and is incorporated by reference in the disclosure of this application.

BACKGROUND OF THE INVENTION

1. Field of the Invention

The invention relates to the field of orally administrable pharmaceutical dosage units; in particular, units in the form of an edible mass, such as a chunk.

2. Background Information

Formulation of a drug into an edible medication, such as a chewable tablet or confection, can increase patient acceptance of the medication, especially animals, who tend to resist swallowing hard tablets or capsules. Unfortunately, many drugs and other active ingredients (collectively, "actives") have a strongly bitter or otherwise unpalatable taste, making chewing them unpleasant.

Flavorings are commonly added to chewable medications to enhance their palatability. For example, a veterinary medication might include animal product-based flavorings such as uncooked dried meat parts such as beef, pork, chicken, turkey, fish and lamb; organ meats such as liver; meat meals, bone meals and ground bone; and animal-derived food such as casein, milk (which may include dry forms and lowered fat forms, such as dry skim milk), yogurt, gelatin, cheese and egg (collectively, "animal origin flavorings") may be utilized.

However, use of many animal origin flavorings (especially of meat, poultry or seafood origin) risks exposure to infectious agents, not only to the recipient of the drug, but also through contamination of manufacturing equipment on which the flavored dosage units are made. For this reason, manufacturing facilities that prepare pharmaceutical products with animal origin flavorings are often devoted exclusively to their preparation, at a correspondingly greater cost than would be incurred if manufacturing could be performed in a facility capable of concurrently processing multiple products.

Texture is also an issue for chewable medications. One of the most commonly used form for chewable dosage units is the compressed tablet, whose ingredients (including the actives and inactive ingredients such as binders) can make the tablet gritty or otherwise unappealing, especially to animals. Thus, a preferred alternative dosage form for use especially with animals is the "edible soft chew," generally a meat-like mass or chunk also widely found in consumable pet treats, having a softness similar to a cooked ground meat patty.

Edible soft chews are typically manufactured by blending and extrusion. Pre-mixed ingredients are introduced into an extruder barrel with a screw therein, then mixed, coagulated, expanded and sheared into a blended mixture, followed by application of additional heat if a harder texture is desired, or water has been introduced into the mixture. Water introduced into the mixture must generally be of pharmaceutical grade, as it will be retained within the mixture. The blended mixture is then formed into a desired shape on a die plate, then cut into individual units.

The heat generated during the extrusion process can cause deterioration in the stability (potency or integrity) of the active in the mixture, causing the effective dose provided by each unit formed to vary. In particular, the heat from compression exerted during extrusion, especially auger extrusion, can exceed the melting point of many compounds. Consistency of texture, shape and weights of the chews from batch to batch of extruded material can also suffer.

There is a need, therefore, for a method of manufacture for edible soft chewable medications in which the blending of actives into the chew mixture is achieved without generation of heat at a level that would cause the active to wholly or partially degrade. Preferably, the method would be performed without application of any heat above room temperature to the mixture or formed product. It is also desirable that the chews be susceptible to manufacture without use of costly, pharmaceutical grade water as an ingredient. There is also a need in the art for a edible soft chew medication whose taste appeals to animals without use of ingredients that may include infectious agents or contaminants. Further, it is highly desirable for the manufacturing means employed to produce chewable medications to do so in a manner that ensures consistent chew weights, texture and active dosages.

SUMMARY OF THE INVENTION

The invention provides a unique edible soft chew dosage form medication and processes for its manufacture. The edible soft chews of the invention are particularly palatable to pet animals. They contain inactive ingredients of at least food grade quality, and most preferably do not contain inactive ingredients of animal origin. As such, the edible soft chews may be manufactured without concern about transmission of infectious agents or contaminants, and without risk of cross-contaminating other products produced in the same manufacturing facility.

The manufacturing processes of the invention allow the edible soft chews to be produced wherein the blending of actives into the chew mixture is achieved without generation of heat at a level that would cause the active to wholly or partially degrade. The method is performed so the chew mixture and formed chews are not exposed to temperatures at or above those typically generated by compression and/or shear stress exerted in extrusion, which may be measured by means known to those of ordinary skill in the manufacturing arts (see, e.g., Vermeulen et al., *Chemical Engineering Science* (1971) 26: 1445-1455; Chung et al., *Polymer Engineering and Science* (1977) 17: 9-20; Mount et al., *Polymer Engineering and Science* (1982) 22(12): 729-737; Lindt, J. T., *Conference Proceedings, ANTEC '84, Society of Plastics Engineers* (1984) 73-76; Rauwendaal, C., Conference Proceedings, ANTEC '93, *Society of Plastics Engineers* (1993) 2232-2237; Miller et al., *Conference Proceedings, ANTEC '74, Society of Plastics Engineers* (1974) 243-246; Derezinski, S. J., *Conference Proceedings, ANTEC '88, Society of Plastics Engineers* (1988) 105-108; Derezinski, S. J., *Journal of Materials Processing & Manufacturing Science* (1997) 6(1): 71-77; Derezinski, S. J., *Conference Proceedings, ANTEC '96, Society of Plastics Engineers* (1996) 417-421).

Preferably, the chew mixture and formed chews are not exposed to temperatures of more than about 10° above room temperature (20° C.), may be exposed to temperatures as low as 0° to about 10° below room temperature, and most preferably are maintained at room temperature throughout the blending and forming steps. As such, the actives in the chew mixture and formed chews are not exposed to heats above or below the temperatures stated during performance of the blending and forming steps, whether by admixture with ingredients at temperatures outside the stated ranges, by application of heat generated by a heat source or compression, or by other means. Stability of the actives is therefore preserved during mixing and formation of the edible soft chews, and a well-blended, soft texture is provided.

No water is used as an ingredient of the chews, thereby avoiding the need for use of costly pharmaceutical grade water, while reducing the opportunity for microbial growth or loss of potency by the active.

It has also been found that admixture of actives with an oil to form a suspension that is then admixed with the dry ingredients of the chew facilitates uniform distribution of the active in the finished product. Preferably, the active will also be coated to conserve the potency of the active prior to admixture with the oil.

For the blending of the coated active suspension with other ingredients of the edible soft chews (e.g., flavorings) a horizontal mixer is preferably used. Such mixers are uniquely well-suited to spins the chew mixture into particulate form. The mixing action causes the ingredients in the mixture to be cast away from the mixing vessel walls, crisscrossing the vessel to provide a uniformly blended mixture formed without application of heat. Because no cooling step is required, the time to produce chews is shortened compared to cooking extrusion methods.

The highly blended mixture produced is placed into molds without extrusion and formed into individual dosage units that are allowed to set without application of heat. Edible soft chews can be produced in any desired shape. Preferred mixing and molding equipment utilized in the invention can provide individual edible soft chews with consistently blended ingredients, stably provided actives and consistent weights.

The edible soft chews of the invention are produced in palatable form without the use of any non-food grade inactive ingredients (or, preferably, any animal origin inactive ingredients). The manufacturing processes may therefore be performed without risk of potential cross-contamination of other equipment in the facility with infectious agents or contaminants derived from sources such as the animal-origin meat flavorings commonly used in chewable medications for animals.

DETAILED DESCRIPTION OF THE INVENTION

A. Materials for Use in Edible Soft Chews of the Invention

In general, edible soft chewable medications and treats include as inactive ingredients matter such as binding agents, vitamins, and colors to enhance the manufacturability, texture and appearance of the product. Those of ordinary skill in the art will be familiar with such inactive ingredients, which need not include water for use in the invention. No inedible ingredients are present within the soft chews.

For use in the invention, no inactive ingredients of the edible soft chew should be of less than food grade quality and may be of higher quality (e.g., USP or NF grade). In this context, "food grade" refers to material that does not contain or impart chemicals or agents hazardous to health. Thus, a food grade flavoring, if of animal origin, will be one that has been prepared to substantially reduce or eliminate the presence of infectious agents or contaminants therein; e.g., by processes such as pasteurization, pressurization or irradiation.

The latter process in particular can effectively eliminate infectious agents such as *E. coli* O157:H7, *Salmonella* and *Campylobacter* from a wide variety of food and animal-derived substances, such as raw meat products, vegetables, grains and fruits. Preferably, however, edible soft chews of the invention will not contain any animal origin ingredients, and most preferably will not contain any animal origin flavorings. All ingredients should be pharmaceutically acceptable (e.g., food grade, USP or NF, as appropriate).

Flavorings are preferably present in edible soft chews of the invention that are at least food grade in quality, and most preferably exclude animal origin flavorings. Preferred non-animal origin flavorings are plant proteins, such as soy protein, to which edible artificial food-like flavorings has been added (e.g., soy-derived bacon flavoring). Depending on the target animal, other non-animal flavorings could include anise oil, carob, peanuts, fruit flavors, sweeteners such as honey, sugar, maple syrup and fructose, herbs such as parsley, celery leaves, peppermint, spearmint, garlic, or combinations thereof.

A particularly preferred flavoring for use in the invention is Provesta™ 356, made by Ohly, Inc. It is a light tan, water-soluble powder that builds on the properties of yeast extracts and reaction flavors to provide a pleasant smoky, cured bacon flavor. Provesta 356 contains no animal derived ingredients.

For administration to horses and other grazing animals, as well as small animals such as rabbits, hamsters, gerbils, and guinea pigs, grains and seeds are especially appealing additional flavoring agents. The grains may be present in any form consistent with the production of the chew including flour, bran, cereal, fiber, whole grain and meal forms, including gluten meals, and may be rolled, crimped, ground, dehydrated or milled. Minerals may also be added as flavorings, such as salt and other spices. Preferably, the grain utilized is dehydrated, milled or flaked. Vegetables such as dehydrated carrots and seeds such as safflower seeds or milo seeds are especially appealing to small animals and may be included.

Further, agents which enhance the manufacturability and texture of a edible soft chew may include softening agents (which may be an anti-sticking agent), an anti-caking agent or lubricant, and a humectant or wetting agent. Illustrative examples of lubricants or anti-caking agents which may be used in the invention include magnesium stearate, calcium stearate, solid polyethylene glycols. If melted, the agents are returned to room temperature +/−10° before admixture with an active, sodium lauryl sulfate, or mixtures thereof. Magnesium stearate is particularly preferred for lubrication and as a component to aid in setting the edible soft chews after molding.

Humectants illustratively include glycerol and propylene glycol, and wetting agents include cetyl alcohol and glycerol monostearate. Glycerin is a preferred humectant useful in maintaining the softness of the edible soft chew over the shelf life of the product. Glycerin is a clear, colorless, odorless, viscous, hygroscopic liquid.

An anti-sticking agent, preferably polyethylene glycol and most preferably PEG 3350 (Dow Chemical), will preferably be included in the edible soft chew mixture before molding at a volume of about 1.0% to 3.0% w/w. After molding, the edible soft chews with the added anti-sticking agent will set-up, usually over a period of 8 to 24 hours for PEG 3350. PEG 3350 congeals quickly, softens the chew mixture, and prevents the edible soft chew units from sticking together after molding.

Softening agents utilized are those which limit density and hardness of the edible soft chew product. Such agents may include polysaccharides and fiber. A polysaccharide may be included in the form of a complex food such as a fruit, a plant starch such as potato or tapioca starch. Polysaccharide may also be provided separately, for example, in the form of chondroitin sulfate or glucosamine HCl.

Fiber may be also provided as filler or as a bulking agent and to provide or maintain porosity in the edible soft chew. Fibers used to this end may be derived from fruits, grains, legumes, vegetables or seeds, or provided in forms such as wood fiber, paper fiber or cellulose fiber such as powdered cellulose fiber. A particularly preferred such bulking agent for use in the invention is bran, such as oat bran.

Binders utilized in edible soft chews may be a sticky substance, but will preferably give the edible soft chew product a food-like texture. In general, binders may include molasses, corn syrup, peanut butter, a starch such as potato starch, tapioca starch or corn starch, honey, maple syrup and sugars. Preferred binders for use in edible soft chews of the invention are starches.

A particularly preferred binder is Starch 1500, a pregelatinized starch made by Colorcon Corporation. Pregelatinized starch is a starch that has been chemically and/or mechanically modified to rupture all or part of the starch granules and so render the starch flowable. It contains 5% of free amylase, 15% of free amylopectin and 80% unmodified starch. The source is from corn.

Powdered sugar (sucrose) serves well as a sweetener as well as a binder. Sucrose is obtained from either sugar cane or sugar beets. Salt and/or other spices may be added as appropriate, with salt being especially preferred to enhance flavor.

A preservative such as potassium sorbate, sodium benzoate or calcium propionate may be included in order to retard growth of microorganisms and fungi. Tenox 4 is a combination of BHA and BHT anti-oxidants, made by Eastman Chemicals. It is a preferred and convenient preservation system.

Vitamins may be provided according to the nutritional requirements of the target animal, and may be provided as an element of oils utilized. Vitamins are also present in various oils that may be added as softening agents; for example, canola oil, corn oil, soybean oil and vegetable oil.

For formation of an active suspension, as well as a flavor enhancer and softening agent, oils are utilized. Vegetable oils (such as corn, safflower, cottonseed, soybean and olive oils) are especially preferred, with soybean oil being most preferred.

Excipients that may be utilized include starches, cellulose, or derivatives or mixtures thereof, in amounts ranging, for example, from about 1 to about 60 percent (w/w), preferably from about 2 to about 50 percent, more preferably from about 15 to 50 percent. For example, the excipient may consist of sodium starch glycolate, pregelatinized corn starch (Starch 1500), crospovidone (Polyplasdone XL™, International Specialty Products), and croscarmellose sodium (Ac-Di-Sol™, FMC Corp.), and derivatives thereof.

Excipients may be used to create a trituration of an active. For example, to create a 10% trituration, 100 grams of the active is combined with 900 grams of an excipient, such as a preferred excipient, Starch 1500. Ideally, a geometric dilution of the active is performed, whereby it is first dissolved in a suitable alcohol solvent; e.g., ethyl alcohol. The dissolved active is then combined with the excipient, and the alcohol allowed to evaporate. This step enables a small amount of active to be comprehensively and evenly mixed throughout the starch. The dry mixture is sifted through a screen mesh, fluidized, and is then preferably coated.

If a coating is to be provided (to help protect the stability of the active and mask its taste), food grade coatings are preferred, such as an aqueous film coat from Colorcon Corporation sold as OPADRY™. OPADRY is a methylcellulose based product with a plasticizer and pigment. Since the coating is aqueous based, no special handling precautions are required during manufacture of the edible soft chew. However, after administration, the aqueous film coat will start to erode and/or dissolve within minutes when exposed to water or other liquids in the stomach. Therefore, disintegration and dissolution of the edible soft chew should not be delayed after it is administered to the subject.

Any orally administrable active drug or other biologically active compound may be provided in the edible soft chews of the invention. However, the invention is uniquely well-suited to use with actives that are heat-labile, especially at temperatures in excess of 30° C. Those of ordinary skill in the human and/or veterinary pharmaceutical arts will be entirely familiar with the identity of such actives which may include, without limitation, antibiotics, analgesics, antivirals, antifungals, anthelmetics, endo- and ecto-parasiticides, hormones and/or derivatives thereof, anti-inflammatories (including non-steroidal anti-inflammatories), steroids, behavior modifiers, vaccines, antacids, laxatives, anticonvulsants, sedatives, tranquilizers, antitussives, antihistamines, decongestants, expectorants, appetite stimulants and suppressants, minerals and vitamins.

The amounts of each of the components in the final product may be varied considerably, depending upon the nature of the drug, the weight and condition of the subject treated, and the unit dosage desired. Those of ordinary skill in the art will be able to adjust dosage amounts for particular actives in the edible soft chews in light of the teachings of this disclosure. Generally, however, the active may be provided by range in weight based on the total weight of the composition from about 0.001% to 75% (w/w), more preferably 0.095% to 40%, and most preferably not in excess of 50%. For example, for administration of an anthelmetic to dogs, such as ivermectin for treatment of heartworms (see, Example 1) triturated with starch could be added to comprise 31.2% of the foregoing mixture.

The formula described for the exemplary product may be easily modified for delivery of actives to other species. For example, equine edible soft chews may be based on the same basic formula, substituting molasses powder, oat bran and apple for the bacon. Flavorings particularly appealing to cats include artificial soy based compounds with a fish-like flavor. Human recipients may prefer sweeter flavorings, such as sugars or molasses.

The edible soft chews of the invention may be packaged individually for administration and stable storage. Examples of suitable packaging materials include HDPE bottles or foil/foil packaging.

B. Processes for Manufacturing Edible Soft Chews of the Invention

Active and inactive ingredients for a edible soft chew of the invention are added to a mixing vessel of a horizontal mixer capable of blending the material and casting it against the side of the mixing vessels. This action permits the ingredients to be well and consistently blended without application of heat or addition of pharmaceutical grade water to the mixture.

Horizontal mixers generally comprise a mixing chamber, an elongated, horizontal mixing shaft which rotates, and a plurality of mixing tools which depend generally perpendicularly from the horizontal shaft to rotate around the inside of the chamber (see, e.g., U.S. Pat. No. 5,735,603, the disclosure of which is incorporated herein by this reference). The mixing tools are configured and dimensioned as required for the mixing process to follow the shape of the chamber walls as rotated for proper mixing of all of material present. Some such mixing chambers are cylindrically shaped, while others are trough-shaped, such as mixers which are commonly referred to in the art as double-arm mixers or ribbon mixers.

In general, a horizontal mixer will have a horizontal mixing shaft extending out of the chamber at both ends. In a motorized mixer, at one end of the shaft, referred to as the drive end, the shaft is operably coupled to a drive motor for rotating the shaft. At the drive end, the shaft is typically coupled through a bearing structure located between the drive motor and the chamber. The bearing structure provides support of the shaft drive end and also ensures smooth rotation. A separate seal structure is often provided further in along the length of the shaft to seal it against leakage of material into and out of the mixing chamber.

A particularly preferred mixer for use in the invention used is a plough type ribbon mixer with optional agitating blades, sold under the FXM Series™ trademark by Littleford Day Corporation. A 200 kg capacity blender can be used for commercial scale production, and is capable of producing as little as 50 kg of chew mixture for research scale work. No heat is applied during mixing, and the blended product produced has a consistent weight, ingredient distribution and texture from batch to batch.

Preferably, dry ingredients of the chew mixture are blended first, then an oil suspension of the active blended therein, followed by admixture with the liquid ingredients (e.g., humectants and softening agents) to form a thoroughly blended mixture. After blending, the chew mixture is discharged without compression from a port through the blender into a suitable container for processing into individual dosage units with a forming machine.

A variety of forming equipment may be utilized in the invention, but those particularly preferred for use are molding machines developed for use in producing molded food products, such as pre-formed hamburger patties and chicken nuggets. For example, the molding machines disclosed in U.S. Pat. Nos. 3,486,186; 3,887,964; 3,952,478; 4,054,967; 4,097,961; 4,182,003; 4,334,339; 4,338,702; 4,343,068; 4,356,595; 4,372,008; 4,535,505; 4,597,135; 4,608,731; 4,622,717; 4,697,308; 4,768,941; 4,780,931; 4,818,446; 4,821,376; 4,872,241; 4,975,039; 4,996,743; 5,021,025; 5,022,888; 5,655,436; and 5,980,228 (the disclosures of which are incorporated herein) are representative of forming equipment that may be utilized in the invention.

Preferred forming equipment for use in the invention are molding machines that do not apply compression heat to the chew mixture, such as the Formax F6™ molding machine made by the Formax Corporation. The F6 machine has the capabilities of 60 stokes per minute. A square forming die of 6" by 6" can be used to form approximately 16 chunk-like edible soft chew units per stroke, each unit weighing 4 grams and being approximately ⅝" by ⅝" in size. Dies for production of other shapes (e.g., bone shaped chews) may also be utilized.

In such a machine, a rotary valve opens to cause the chew mixture to flow through fill slots beneath into a first set of mold cavities. A mold plate is advanced, forcing the chew mixture into a second set of cavities, then the mold plate is retracted so the cycle can begin again. The molding mechanism is hydraulic, and works by light pressure on the molding plate, without application of heat.

A knockout mechanism is provided with cups that align with the cavities to eject molded mixture from all the mold plate cavities simultaneously. For molding edible soft chews of the invention, such a machine could produce an output per hour of approximately 57,600 units, assuming use of a blender mixture yielding 50,000 units per sub batch. Each batch of chews may be packaged in bulk or, preferably, each chew is then individually packaged for storage.

The invention having been fully described, its practice is illustrated by the examples provided below. Standard abbreviations and measurements apply throughout the examples unless a contrary definition is given. The examples do not limit the scope of the invention, which is defined entirely by the appended claims.

EXAMPLE 1

Edible Soft Chew Formulation

An example of a edible soft chew suitable for delivery of an active is set forth in Formula 1 below.

| Formula 1: | |
|---|---|
| Concentration % w/w | Ingredient |
| 44.69 | Starch 1500, USP |
| 19.0 | Bacon Flavor (Provesta ™ 356), Food Grade |
| 2.0 | Polyethylene glycol 3350 |
| 20.0 | Glycerin, USP |
| 7.0 | Vegetable Oil (soybean), USP |
| 0.1 | Tenox 4, Food Grade |
| 1.0 | Magnesium Stearate, USP |
| 1.0 | Yeast Flavoring |
| 5.0 | Croscarmellose, sodium N.F. |
| 0.2 | Sodium lauryl sulfate |
| 0.001 | FD&C Carmine Dye |

EXAMPLE 2

Method For Coating Active Ingredients of Edible Soft Chews of the Invention

A 10% trituration of active (ivermectin) was made by dissolving 100 grams of ivermectin into ethyl alcohol, then mixing the active in 900 grams of Starch 1500 for 3 to 5 minutes. The resultant trituration was allowed to stand until dry, then milled and screened through a 20 mesh screen. The screened trituration was fluidized in a fluidized bed column. A food grade coating (OPADRY™) was applied to the triturated active using a Wurster coater. A top spray fluidized coater, or other suitable device, could also be used for this step. The coated active was then admixed in soybean oil to form a suspension.

EXAMPLE 3

Exemplary Method of Manufacture For Edible Soft Chews of the Invention

All dry ingredients listed in Examples 1 and 2 were sifted through a 20 mesh screen, then placed into the mixing vessel of a horizontal mixing blender and mixed for 5 minutes. The glycerin was added slowly followed by the slow addition of the vegetable oil/active suspension, and Tenox 4 which had been added to the oil. The product was mixed for 3 minutes. The PEG 3350 was melted then added relatively quickly to the chew mixture, which was then mixed for an additional minute. The mixture resembled a "cookie dough-like" appearance.

The mixture was formed into individual chunks using a Formax F6™ molding machine with dies for production of chunk-like shapes, and packaged for storage.

The invention having been fully described, its scope is defined by the claims appended hereto.

What is claimed is:

1. A process for manufacturing a palatable soft chewable pharmaceutical product (a "soft chew") having consistent unit-to-unit weight and active content without use of extrusion, comprising:
    (a) providing at least one active agent whose stability or potency can be adversely affected by temperatures typically generated during extrusion, an active agent that is not palatable, or both;
    (b) blending the active agent with dry inactive ingredients under low shear conditions to produce a edible soft chew mixture having the active agent uniformly blended therein;
    (c) adding anon-aqueous fluid to the dry mixture and blending it under low shear conditions to form an edible soft chewable mixture; and,
    (d) forming the edible soft chewable mixture into soft chews without application of compression heat thereto, wherein the edible soft chew mixture and the ingredients thereof are maintained at room temperature or no more than +1/−10° C. thereof during performance of each step of the process; and,
wherein further the soft chews are more palatable than tablet dosage forms of the active agent.

2. The process according to claim 1, wherein the active is selected from the group of actives consisting of is selected from the group of ingredients consisting of anthelmetics, analgesics, antibiotics, antithyroids, antivirals, anti-inflammatories, endoparasiticides, ectoparasiticides and antifungals.

3. The process according to claim 1, wherein the active is one whose potency or stability is adversely affected at temperatures 10° C. over or under room temperature.

4. The process according to claim 1, wherein the dry inactive ingredients comprise at least one flavoring and at least one excipient.

5. The process according to claim 3, wherein the excipient comprises starch.

6. The process according to claim 1, wherein the dry active ingredients comprise at least one bulking agent.

7. The process according to claim 6, wherein the bulking agent comprises bran, meal, flour, cereal, fiber, whole grains, vegetables, seeds, gum arabic, pectins, modified starches, alginates, carrageenans, xanthan gums, carboxymethylcellulose, methylcellulose, hydroxyethylcellulose, hydroxypropylcellulose, propylene glycol alginate, polyvinylpyrrolidone, carboxyvinyl polymers, polyethylene oxide polymers, talc, dicalcium phosphate or antacids.

8. The process according to claim 1, wherein the non-aqueous fluid is an oil.

9. The process according to claim 1, further comprising the step of preparing a trituration of the active ingredient with an excipient before the active ingredient is added to the dry inactive ingredients.

10. The process according to claim 1, wherein the active provided is coated.

11. The process according to claim 2, wherein the at least one active is an antibiotic.

12. The process according to claim 11, wherein the active is milbemycin, clindamycin, enrofloxacin, cefpodoxime, ivermectin or amoxicillin.

13. The process according to claim 2, wherein the active is lufenuron.

14. The process according to claim 2, wherein the active is praziquantal.

15. The process according to claim 2, wherein the active is methiamazole.

16. The process according to claim 2, wherein the active is imidacloprid.

17. A finished soft chew produced by the process of claim 1.

* * * * *